US011326968B2

(12) United States Patent
Halse et al.

(10) Patent No.: US 11,326,968 B2
(45) Date of Patent: May 10, 2022

(54) DEVICES AND METHODS FOR DETECTING AXIAL FORCES APPLIED TO A CONTAINER

(71) Applicant: Smart Skin Technologies Inc., Fredericton (CA)

(72) Inventors: Jonathan Halse, Saint Andrews (CA); Abhishek Kar, Fredericton (CA); Jordan Ritchie, Island View (CA); Shawn Maurice Dale Durette, Yoho (CA); Daniel Robert Rogers, McLeod Hill (CA)

(73) Assignee: Smart Skin Technologies Inc., Fredericton (CA)

( * ) Notice: Subject to any disclaimer, the term of this patent is extended or adjusted under 35 U.S.C. 154(b) by 121 days.

(21) Appl. No.: 16/927,819

(22) Filed: Jul. 13, 2020

(65) Prior Publication Data
US 2022/0011182 A1 Jan. 13, 2022

(51) Int. Cl.
*G01L 5/00* (2006.01)
*G01L 1/22* (2006.01)
*A61M 5/24* (2006.01)

(52) U.S. Cl.
CPC .............. *G01L 5/0028* (2013.01); *G01L 1/22* (2013.01); *A61M 5/24* (2013.01)

(58) Field of Classification Search
CPC ........... G01L 5/0028; G01L 1/22; A61M 5/24
See application file for complete search history.

(56) References Cited

U.S. PATENT DOCUMENTS

| | | | | |
|---|---|---|---|---|
| 3,771,649 A | * | 11/1973 | Strauss | G01N 3/12 209/3.1 |
| 4,144,742 A | * | 3/1979 | Schmidt | G01N 3/12 141/105 |
| 4,788,850 A | * | 12/1988 | Buschor | G01M 3/3236 73/37 |
| 4,989,462 A | | 2/1991 | Davis et al. | |

(Continued)

FOREIGN PATENT DOCUMENTS

CN 105628274 A 6/2016

OTHER PUBLICATIONS

International Search Report and Written Opinion dated Oct. 14, 2021 in related International Patent Application No. PCT/CA2021/050938 (7 pages).

*Primary Examiner* — Max H Noori
(74) *Attorney, Agent, or Firm* — Bereskin & Parr LLP/S.E.N.C.R.L., s.r.l.

(57) ABSTRACT

Devices and methods for detecting axial forces applied to a container are provided. The devices can include a device housing, a container section, a force measurement sensor, and a processing section. The device housing can extend between a first housing end and a second housing end along a longitudinal axis. The container section can be mounted to the housing proximate the first housing end. The container section can have an open first section end and a closed second section end spaced apart along the longitudinal axis and at least one sidewall extending therebetween. The container section can define a cavity bounded by the first section end, the second section end and the at least one sidewall. The force measurement sensor can be positioned to generate the force measurement data in response to an axial force applied at the first section end.

24 Claims, 8 Drawing Sheets

(56) References Cited

U.S. PATENT DOCUMENTS

| | | |
|---|---|---|
| 2010/0147822 A1 | 6/2010 | Burrows et al. |
| 2017/0343395 A1 | 11/2017 | Woernle et al. |
| 2021/0093784 A1* | 4/2021 | Adams ................ A61M 5/3137 |
| 2021/0339594 A1* | 11/2021 | Wang ................ B60G 17/0152 |
| 2021/0346618 A1* | 11/2021 | Mikosz ............. A61M 15/0025 |

* cited by examiner

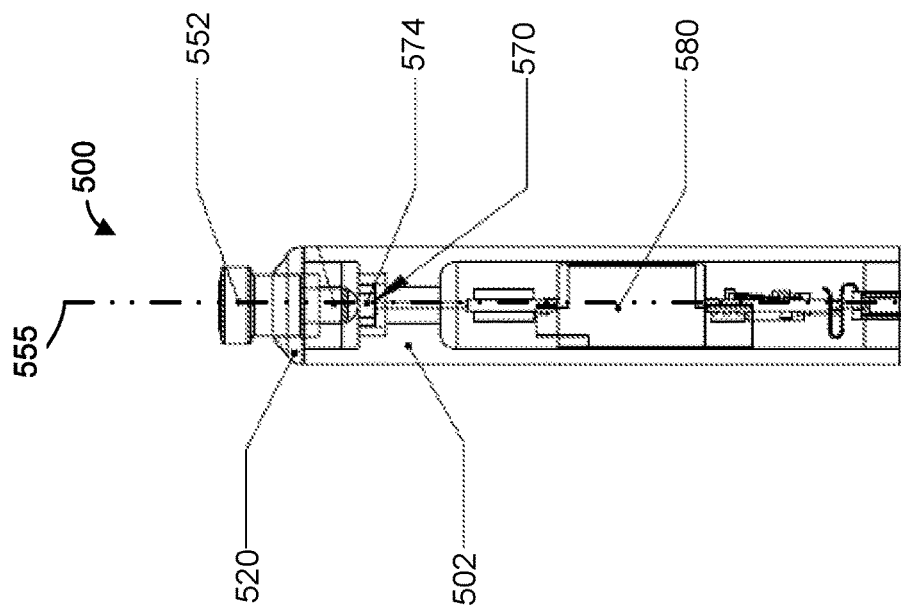
FIG. 5C
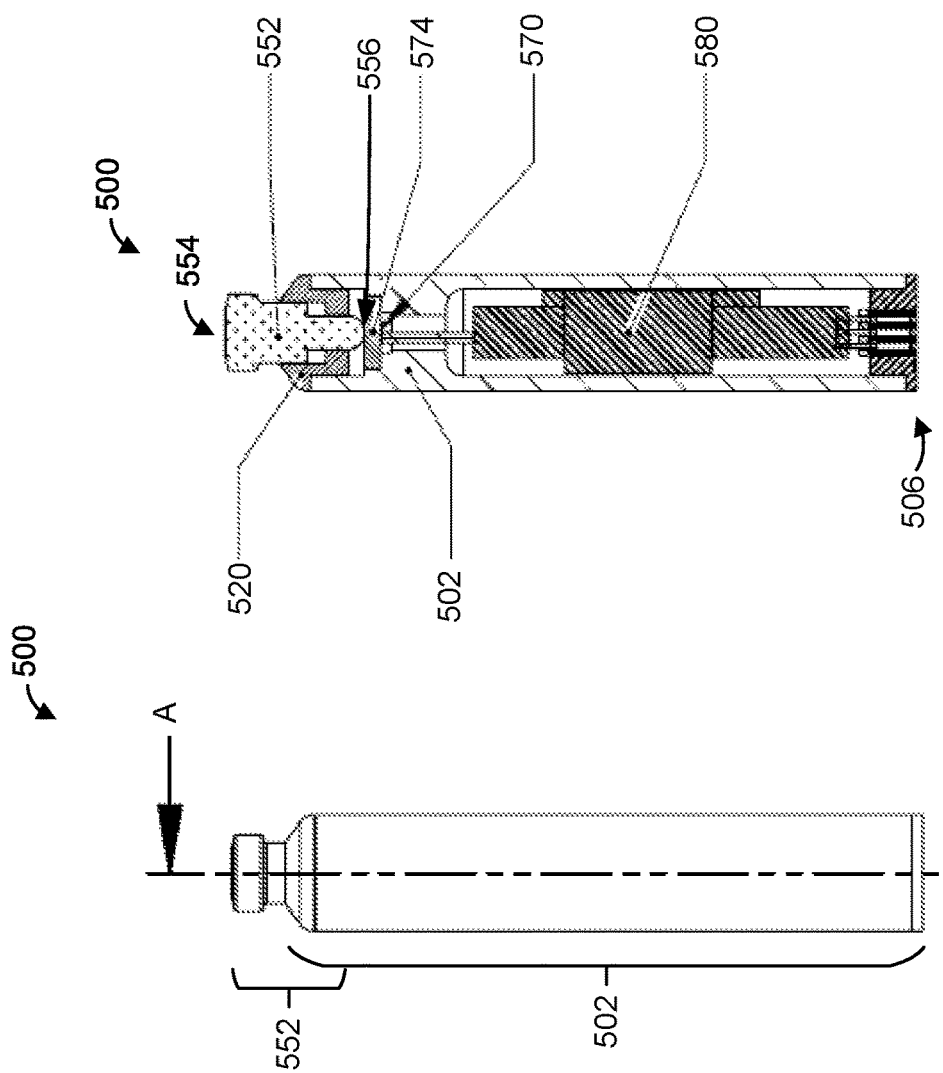
FIG. 5B
FIG. 5A

DEVICES AND METHODS FOR DETECTING AXIAL FORCES APPLIED TO A CONTAINER

FIELD

The embodiments described herein generally relate to detecting forces, and in particular to detecting axial forces applied to a container.

BACKGROUND

The following is not an admission that anything discussed below is part of the prior art or part of the common general knowledge of a person skilled in the art.

Containers can be used to house a product during distribution, storage, sale, and/or use. A container can provide physical protection for the product stored therein. For example, the container may protect the product from damage that may be caused by mechanical shock, compression, vibration, or other forms of energy transfer. The container may also act as a barrier to heat, oxygen, humidity, dust, bacteria, and/or other undesirables. The container can reduce the risk of degradation or contamination and enhance the shelf life and safety of the product.

At various stages of production, transportation and distribution, the container may be subject to potentially damaging forces. For example, a production line may include equipment or machinery for filling, sealing, labeling, and/or transporting the container. Each stage in the production line may involve some physical contact (direct or indirect) between the equipment and the container that could potentially result in damage. Similarly, during shipping, the container may experience various physical forces, as the container is physically transported to a destination.

Modern production and transportation processes may be highly optimized to reduce the risk of damage to a container to low levels. However, when damage is detected, it can be difficult to identify the source of the damage along the production and transportation process. Continuing to produce damaged containers can be costly, as the damaged containers may be difficult or impossible to sell. In some cases, damaged containers may also pose a danger to other products or to people or animals, for instance if the product contents are potentially hazardous.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

The various embodiments described herein generally relate to devices and methods for detecting axial forces applied to a container. The axial forces may be sensed while the container is undergoing a production, distribution, and/or transportation process.

In accordance with an aspect of this disclosure, there is provided a device for detecting axial forces applied to a container. The device can include a device housing, a container section, a force measurement sensor, and a processing section. The device housing can extend between a first housing end and a second housing end along a longitudinal axis. The device housing can have an inner housing wall and an outer housing wall. The container section can be mounted to the housing proximate the first housing end. The container section can have an open first section end, a closed second section end, and at least one sidewall extending between the first section end and the second section end. The container section can define a cavity bounded by the first section end, the second section end and the at least one sidewall. The first end can be spaced apart from the second end along the longitudinal axis. The force measurement sensor can be positioned within the device housing. The force measurement sensor can be configured to generate force measurement data. The processing section can be positioned within the housing. The processing section can include a processor and a battery. The processor can be configured to receive the force measurement data from the sensor. The battery can be configured to supply electrical power the processor. The force measurement sensor can be positioned to generate the force measurement data in response to an axial force applied at the first section end.

In any embodiment, the force measurement sensor can be positioned proximate the second section end.

In any embodiment, the container section can be movable towards the second housing end along the longitudinal axis in response to force applied at the first section end. The force measurement sensor can be positioned to deflect in response to motion of the second closed end towards the second housing end and to generate the force measurement data in response to the deflection.

In any embodiment, the device can further include a mounting unit fixedly secured to the housing between the inner housing wall and the container section. The mounting unit can be configured to receive the container section and to constrain the longitudinal motion of the container section.

In any embodiment, the mounting unit can include a bearing sleeve.

In any embodiment, the mounting unit can include a sealing member configured to engage the container section and to seal the container section to the mounting unit.

In any embodiment, the sealing member can be configured to impede ingress of fluid into the housing.

In any embodiment, the mounting unit, container section and housing can be concentric.

In any embodiment, the force measurement sensor can be positioned between the container section and the processing section.

In any embodiment, the force measurement sensor can be spaced apart from the processing section.

In any embodiment, the device can further include a support member extending between the force measurement sensor and the processing section. The support member can support the force measurement sensor adjacent to the second section end.

In any embodiment, the processor can be provided by a printed circuit board, and the battery can be positioned between the printed circuit board and the force measurement sensor.

In any embodiment, the device housing can include at least one aperture at the second housing end. The at least one aperture can define a channel from the second housing end to the printed circuit board.

In any embodiment, the force measurement sensor can include a load cell.

In any embodiment, the load cell can include a button extending from the load cell toward the second section end. The button can be positioned to deflect in response to movement of the second section end towards the second housing end.

In embodiment, the first section end can be configured to receive a closure member configured to seal the cavity.

In any embodiment, the first section end can include a rigid material.

In any embodiment, the processing section can further include a communication interface configured to transmit the force measurement data to an analysis system.

In any embodiment, the processing section can further include a data storage unit configured to store the force measurement data.

In any embodiment, the data storage unit can be configured to store calibration data specific to the device. The processor can be configured to calibrate the force measurement data generated by the force measurement sensor using the calibration data.

In any embodiment, the device can further include an accelerometer, positioned within the housing, configured to detect acceleration of the device and generate acceleration measurement data in response.

In any embodiment, the housing can have an inner housing diameter of at most 50 mm.

In any embodiment, the container section, processing section, and the force measurement sensor can be arranged linearly within the housing.

In any embodiment, the second housing end can include an extendable section configured to extend and retract along the longitudinal axis to adjust a longitudinal length of the extendable section.

In any embodiment, the extendable section can include a fixed section and a rotatable portion rotatably mounted to the fixed section. When the rotatable portion is rotated in a first direction, the extendable section can extend along the longitudinal axis increasing the longitudinal length of the extendable section. When the rotatable portion is rotated in a second direction, the extendable section retracts along the longitudinal axis, decreasing the longitudinal length of the extendable section.

In any embodiment, the force measurement sensor can include a strain gauge.

In any embodiment, the strain gauge can include a strain element positioned to deform in response to motion of the second closed end towards the second housing end. The strain gauge can be configured to generate the force measurement data in response to the deformation of the strain element.

In any embodiment, the container section can be configured to deform in response to the axial force applied to the container section. The strain gauge can be configured to generate the force measurement data in response to the deformation of the container section.

In accordance with an aspect of this disclosure, there is provided a method for measuring axial sealing forces using the device. The method can involve: applying a closure member to the first section end to seal the cavity; generating force measurement data in response to the application of the closure member; and determining an axial force of the application of the closure member using the force measurement data.

In any embodiment, the method can further involve replacing the container section having a longitudinal length with another container section having a different longitudinal length so that the device has a desired overall longitudinal length.

In any embodiment, the second housing end can include an extendable section configured to extend and retract along the longitudinal axis to adjust a longitudinal length of the extendable section. The method can further involve adjusting the longitudinal length of the extendable section by one of extending and retracting the extendable section so that the device has a desired overall longitudinal length.

In any embodiment, the method can further involve inserting a product into the cavity prior to applying the closure member.

In any embodiment, the method can further involve generating additional force measurement data in response to the insertion of the product into the cavity; and determining an additional axial force of the insertion of the product using the additional force measurement data.

In accordance with an aspect of this disclosure, there is provided a device for detecting axial forces applied to a container. The device can include a device housing, a container section and a force measurement sensor. The device housing can extend between a first housing end and a second housing end along a longitudinal axis. The device housing can have at least one sidewall extending between the first housing end and the second housing end. The container section can be mounted to the housing proximate the first housing end. The container section can have an open first section end, a closed second section end, and at least one sidewall extending between the first section end and the second section end. The container section can define a cavity bounded by the first section end, the second section end. The force measurement sensor can be positioned within the device housing. The force measurement sensor can be configured to generate force measurement data. The force measurement sensor can be positioned to generate the force measurement data in response to an axial force applied at the first section end.

In accordance with an aspect of this disclosure, there is provided a device for detecting axial forces applied to a container. The device can include a device housing, a container section, a force measurement sensor, and a processing section. The device housing can extend between a first housing end and a second housing end along a longitudinal axis. The device housing can have an inner housing wall and an outer housing wall. The container section can be mounted to the housing proximate the first housing end and extend into the device housing. The container section can have an open first section end, a closed second section end, and at least one sidewall extending between the first section end and the second section end. The container section can define a cavity bounded by the first section end, the second section end and the at least one sidewall. The first end can be spaced apart from the second end along the longitudinal axis. The force measurement sensor can be positioned within the device housing. The force measurement sensor can be configured to generate force measurement data. The processing section can be positioned within the housing. The processing section can include a processor and a battery. The processor can be configured to receive the force measurement data from the sensor. The battery can be configured to supply electrical power the processor. The force measurement sensor can be positioned to generate the force measurement data in response to an axial force applied at the first section end.

It will be appreciated that the aspects and embodiments may be used in any combination or sub-combination. Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which:

FIG. 5A is a side view of another example axial force measurement device in accordance with an embodiment;

FIG. 5B is a cross-sectional view of the axial force measurement device shown in FIG. 5A taken along line A-A in FIG. 5A;

FIG. 5C is a transparent side view of the axial force measurement device shown in FIG. 5A.

Figure 1:
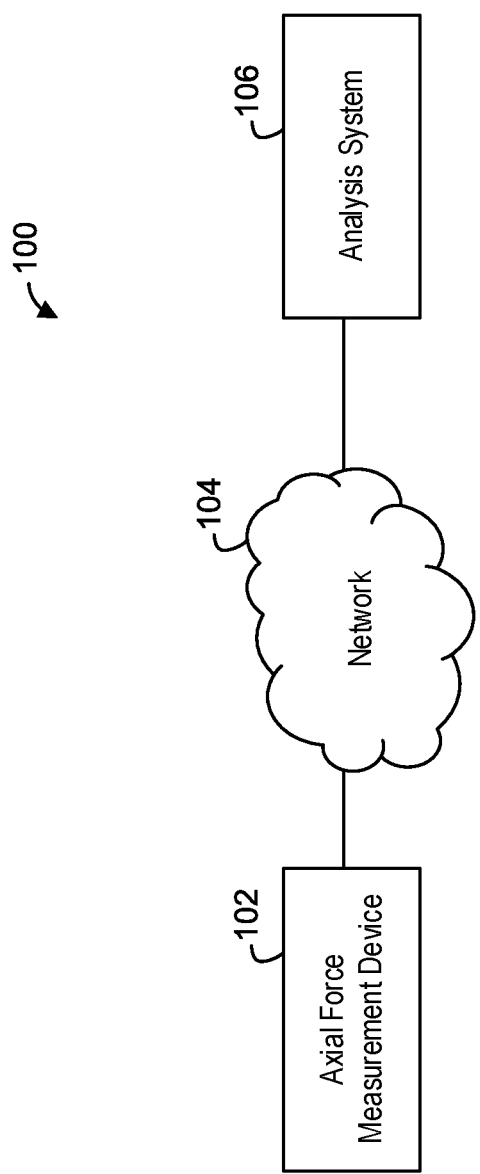
FIG. 1 is a block diagram of an example container monitoring system in accordance with an embodiment.

The skilled person in the art will understand that the drawings, described below, are for illustration purposes only. The drawings are not intended to limit the scope of the applicants' teachings in any way. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more elements are said to be "coupled", "connected", "attached", or "fastened" where the parts are joined or operate together either directly or indirectly (i.e., through one or more intermediate parts), so long as a link occurs. As used herein and in the claims, two or more elements are said to be "directly coupled", "directly connected", "directly attached", or "directly fastened" where the element are connected in physical contact with each other. None of the terms "coupled", "connected", "attached", and "fastened" distinguish the manner in which two or more elements are joined together.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers may be a server, network appliance, embedded device, computer expansion module, a personal computer, laptop, personal data assistant, cellular telephone, smartphone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high-level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

During a production and transportation process, a container may be subject to a number of forces that can potentially damage the container. Depending on the severity of the damage, it may not be possible to sell the container, for example, due to regulatory and/or customer requirements. Identifying the source(s) of damage and assessing the severity of damage in the production and transportation process can be crucial in minimizing or preventing damage to container in the future. This can help maximize production yields and minimize lost costs.

It is often difficult to precisely identify the source of damage to a container along the chain of a production and transportation process. The production process for a container can be extremely complex and may include multiple production steps involving various pieces of equipment or machinery. Inspecting each manufacturing step and each corresponding piece of equipment in the production process can be time consuming and may result in costly downtime in the production process. The transportation process for a container may be equally complex, for example, involving multiple different couriers and modes of transport over large geographical areas and extended periods of time.

Identifying and assessing specific types of forces applied to a container during a production and transportation process may aid in the identification and assessment of potential source(s) of damage. The measurement of axial forces applied to a container is often of particular interest. Axial forces can be defined as forces acting generally or primarily along the longitudinal axis of a container. The detection of axial forces may be helpful in identifying problems associated with various aspects of a production and transportation process, such as filling, sealing, or capping containers for example. However, it may be difficult to detect axial forces applied to a container, particularly when the container has a small form factor. For example, it may be difficult to measure axial forces applied to pharmaceutical containers, such as syringes, cartridges, vials, pens, ampules, and the like due to their small size. In particular, small form factor containers may have limited internal volumes for housing sensors and other electronics.

Embodiments described herein provide devices and methods for detecting axial forces applied to a container. The devices described herein may be implemented with actual containers and/or replica containers (also referred to as drones). The devices can be configured to detect and/or monitor axial forces applied to the containers. This may allow a production and/or transportation process to be evaluated with minimal disruption to the normal operating process.

In embodiments where the force sensing devices are configured as replica containers, the replica containers can be configured to mimic various properties of an actual container, including, but not limited to, the general shape and form of the container. For example, the device may emulate the form factor of containers that are relatively small in size, such as pharmaceutical containers. The device may be substituted for an actual container and undergo one or more stages of a production and/or transportation process intended for the actual container. The device can measure various axial forces during the production and/or transportation process.

In embodiments described herein, the device can include a container section and a device housing section. In some examples, the container section can be configured to provide an internal volume and/or cavity within which a product may be received. Alternately, the container section can be configured to mimic an actual container and may omit the internal volume. The device can be configured to measure various axial forces that may be received by the container section.

The device housing can house various electronics that may be usable to measure the axial forces applied to the container section. For example, the device housing may house one or more sensors configured to generate force measurement data in response to axial forces applied to the container section. Optionally, the device housing may partially or wholly house the container section. Alternately, the container section may be coupled to an end of the device housing.

In embodiments described herein, the device may use a relatively small number of sensors to mimic containers with a small form factor, such as pharmaceutical containers. In embodiments described herein, the axial force measurement device can be configured to accurately measure axial forces even with a limited number of sensors. In some examples, an axial force measurement device may include only a single sensor. For instance, the axial force measurement device may include a single load cell or a single strain gauge.

The embodiments described herein can be used to identify problems in a production and transportation process, such as faulty or unreliable equipment that can cause damage to articles. The impact sensing systems described herein may be used to optimize production and transportation processes for a product, by minimizing the damage to the product and/or package. This can help maximize production yield.

Referring now to FIG. 1, there is shown a block diagram of a container monitoring system 100. As shown in the example of FIG. 1, the container monitoring system 100 can include an axial force measurement device 102, an analysis system 106, and a network 104.

The axial force measurement device 102 can be a container for which axial forces are desired to be measured. The container can be configured to store a product for storage, transportation, sale etc. The container can be configured to store various different types of products, such as liquid (e.g. medicines, beverages, other types of liquids etc.), or solid (e.g. powders, tablets, cartridges, other types of solids etc.) products for example. The axial force measurement device 102 can be configured to detect and measure axial forces applied to the container (or replica). For example, the axial force measurement device 102 can be configured to detect and measure axial forces applied to a container expected to undergo a production and/or transportation process.

Alternately, the axial force measurement device 102 may be a replica of the container for which axial forces are desired to be measured. The axial force measurement device 102 can mimic various properties of an actual container. For example, the axial force measurement device 102 can have the same or similar shape, size, and/or weight as the actual container. The axial force measurement device 102 may have the same or similar mechanical properties as the actual container, such as, but not limited to, strength, ductility, hardness, impact resistance, or fracture toughness.

In some examples, the device 102 may include a container or replica of a container having a relatively small form factor. For example, the axial force measurement device 102 may be a replica of a pharmaceutical container, such as, but not limited to, a bottle, a vial, a syringe, a cartridge, a vial, a pen, or an ampule. Several different examples of axial force measurement devices 102 having different form factors will be described in greater detail with reference to FIGS. 2, 3, 5, and 6.

The axial force measurement device 102 can be configured to detect axial forces applied to the device 102. The axial force measurement device 102 can include one or more sensors. The one or more sensors can produce force measurement data in response to axial forces applied to the device 102.

The axial force measurement device 102 can communicate with an analysis system 106 via the network 104. The network 104 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these, capable of interfacing with, and enabling communication between, the axial force measurement device 102 and analysis system 106.

The axial force measurement device 102 can send and receive various data to and from the analysis system 106 via the network 104. For example the axial force measurement device 102 may transmit data related to axial forces applied to the device 102 to the analysis system 106.

The analysis system 106 may communicate with a plurality of axial force measurement devices 102. The analysis system 106 may receive force measurement data associated with and from each device 102. Although only one axial force measurement device 102 is shown in FIG. 1 for ease of illustration, the container monitoring system 100 can include any number of axial force measurement devices 102, each operable to sense axial forces applied to that device 102 and communicate with the analysis system 106.

The axial force measurement device 102 can provide force measurement data to analysis system 106. This may allow the analysis system 106 to further evaluate the nature of the axial forces applied to the device 102. For example, the axial force measurement device 102 may transmit force measurement data using a wired or wireless communication interface. Alternately or in addition, the force measurement data may be stored in a data storage on axial force measurement device 102. The force measurement data may then be retrieved from the axial force measurement device 102 and provided to analysis system 106. The analysis system 106 may then process or evaluate the force measurement data to determine various characteristics of the axial forces.

The analysis system 106 can perform various processing on the data received from the axial force measurement devices 102. In some examples, the analysis system 106 may calibrate the force measurement data based on one or more calibration parameters associated with a particular axial force measurement device 102. In some cases, the analysis system 106 may store the calibration parameters associated with each axial force measurement device 102. For example, the calibration parameters for a particular axial force measurement device 102 may be determined based on an initial calibration assessment of the device 102. The results of the initial calibration assessment may then be used to determine the calibration parameters that can be stored in analysis system 106. Alternately or in addition, the calibration parameters may be stored in memory on the device 102 itself.

In some examples, the analysis system 106 may correlate force measurement data with steps or locations along a production and/or transportation process. For instance, the force measurement data may be associated with device location data. The device location data may define a location of the article directly, e.g. using position tracking techniques such as GPS or more local position tracking techniques using RFID signals, Bluetooth, or Wi-Fi. Alternately or in addition, the device location data may include data usable to infer the device location, such as the date and/or time at which the force measurement data was generated. The analysis system 106 can then correlate the device location data and force measurement data to identify portions of the production and/or transport process involving axial forces. In some cases, the analysis system 106 may generate aggregate reports and/or visualizations based on data associated with a plurality of different axial force measurement devices 102.

The analysis system 106 may include a processor, a data storage, and a communication interface. The analysis system 106 can include computer-executable instructions stored in the data storage that can be executed by the processor to configure the processor to perform various analysis processes. The analysis system 106 may be provided using various computing such as, for example, an electronic tablet device, a personal computer, workstation, server, portable computer, mobile device, personal digital assistant, laptop, smart phone, WAP phone, an interactive television, video display terminals, gaming consoles, and portable electronic devices etc. In some cases, the analysis system 106 can be provided by multiple components over a wide geographic area.

Optionally, some or all of the analysis performed by the analysis system 106 may be performed locally at the axial force measurement device 102. In some cases, the axial force measurement device 102 may process the force measurement data and transmit the processed data to the analysis system 106. For example, device 102 may include a processor and memory storing computer-executable instructions usable to configure the processor to perform various analysis operations.

Figure 2:
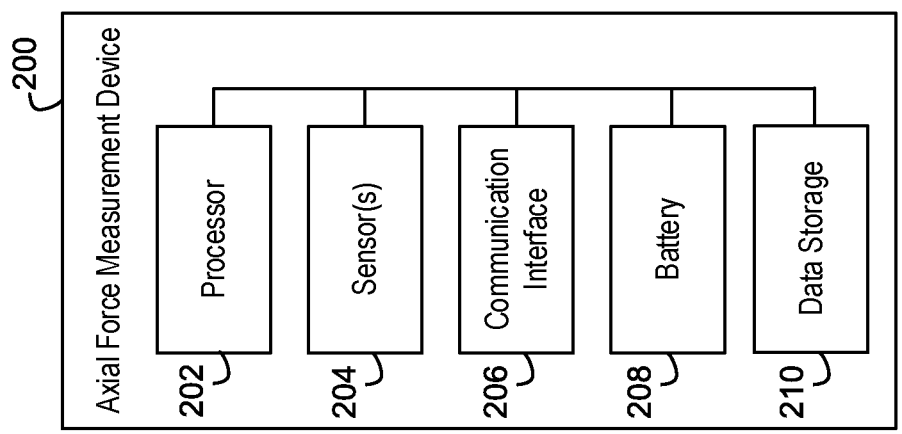
FIG. 2 is a block diagram of an example axial force measurement device in accordance with an embodiment.

Referring now to FIG. 2, there is shown a block diagram of an example axial force measurement device 200. The example axial force measurement device 200 may be used in various force measurement systems, such as an implementation of the axial force measurement device 102 of system 100. As shown in the example of FIG. 2, the axial force measurement device 200 can include a processor 202, one or more sensors 204, a communication interface 206, a battery 208, and a data storage unit 210.

The sensor(s) 204 can include one or more axial force measurement sensors usable to detect and/or measure axial forces applied to the axial force measurement device 200. The axial force measurement sensors can be configured to generate force measurement data in response to axial forces applied to the axial force measurement device 200. For example, the axial force measurement sensors 204 may include one or more load cells (such as Honeywell 834M1 series load cells or Futek LLB130 load cells) and/or strain gauges.

In some cases, the axial force measurement device 200 can include various additional sensor(s) 204. The additional sensors can include different types of sensors (other than axial force measurement sensors) usable to measure other properties of the device 200 and/or environment in which the device 200 is located and/or forces applied to the device. In some examples, the axial force measurement device 200 can include one or more sensors configured to detect and/or measure impact, pressure, acceleration, orientation, location etc. For instance, the axial force measurement device 200 can include an accelerometer configured to detect acceleration of the device 200 and in response, generate acceleration measurement data. In some embodiments the sensor(s) 204 can include gyroscope for measuring the spin of the axial force measurement device 200.

The processor 202 may be any suitable processors, controllers, digital signal processors, or application specific circuitry that can provide sufficient processing power depending on the configuration, purposes and requirements of the axial force measurement device 200. In some embodiments, the processor 202 can include more than one processor with each processor 202 being configured to perform different dedicated tasks.

The processor 202 can be configured to control the operation of the axial force measurement device 200. For example, the processor 202 can control operation of the sensor(s) 204. The processor 202 can also be configured to control communications between the axial force measurement device 200 and external devices, such as the analysis system 106.

In some examples, the processor 202 may be configured to process force measurement data received from the sensor (s) 204. For example, processor 202 may be configured to process the data received from the sensors 204 to determine an axial force applied to the device 200. Alternately or in addition, processor 202 may be configured to calibrate the force measurement data (and/or applied axial force) based on one or more calibration parameters for the device 200. For example, calibration parameters may be stored in data storage 210. Processor 202 may use the stored calibration parameters to adjust/calibrate the force measurement data based on the specific parameters of the given device 200.

Alternately, processor 202 may not perform any processing on the received force measurement data. For example, processor 202 may store and/or transmit the force measurement data without any processing and/or adjustments.

In some examples, processor 202 may be configured to store the force measurement data received from the sensor(s) 204 in data storage 210. Processor 202 may store the force measurement data in data storage 210 in an unprocessed form. Alternately or in addition, processor 202 may be configured to store processed force measurement data (e.g. calibrated force measurement data) and/or determined axial force data in data storage 210.

In some examples, processor 202 may be configured to transmit the force measurement data to an external analysis system, such as system 106. Processor 202 may transmit the force measurement data to external devices using communication interface 206. Alternately, the processor 202 may simply receive the force measurement data and provide the data to the communication interface 206 in an unprocessed form (i.e. without performing any processing on the received force measurement data). Alternately or in addition, processor 202 may be configured to provide processed force measurement data (e.g. calibrated force measurement data) and/or determined axial force data to an external analysis system using communication interface 206.

The communication interface 206 may be any interface that enables the axial force measurement device 200 to communicate with other devices and systems, such as, but not limited to, an analysis system 106 using a network such as the network 104. In some embodiments, the communication interface 206 can include at least one of a serial port, a parallel port or a USB port. The communication interface 206 may also include at least one of an Internet, Local Area Network (LAN), Ethernet, Firewire, modem or digital subscriber line connection. In some embodiments, the communication interface 206 may be a wireless communication interface, which can transmit various data to other devices or systems via Bluetooth, WiFi, or other suitable wireless communication standard. In some cases, the communication interface 206 may be omitted. For example, where the data storage 210 is a removable data storage device, the communication interface 206 may not be needed.

In some embodiments, the communication interface 206 may include a visual indicator, such as, but not limited to, a LED or other light source. The visual indicator can provide a visual representation of the force measurement data. For example, a LED may be configured to emit light when a force detected by the device 200 exceeds a predetermined magnitude. The visual indicator may provide a rapid evaluation of the force measurement data to a user, without requiring external transfer of the force measurement data from the device 200. In some cases, the visual indicator may be configured to emit a plurality of different light signals (e.g. different light patterns and/or colors). Each signal may be defined to correspond to a level of force detected by the device (e.g. green for low levels of force, yellow for medium levels of force, and red for high levels of force).

The data storage 210 may store various data, such as, but not limited to force measurement data from the sensors 204. In some cases, the data storage 210 may store calibration data specific to the device 200 that can be used to calibrate the force measurement data. The data storage 210 may also store processed data determined by the processor, such as calibrated force measurement data and/or determined axial force data. The data storage 210 can include RAM, ROM, one or more hard drives, one or more flash drives or some other suitable data storage elements such as disk drives, etc. In some cases, the data storage 210 may be removable from the axial force measurement device 200.

The battery 208 can provide electrical power to various components of the axial force measurement device 200, such as, the processor 202, the sensor(s) 204, the communication interface 206, and the data storage 210. In some cases, the battery 208 may be a rechargeable battery.

Referring now to FIGS. 3A-D, there is shown an example axial force measurement device 300. In the example illustrated in FIGS. 3A-D, the axial force measurement device 300 can be a replica of a container in the form of a pharmaceutical bottle.

Figure 3A:
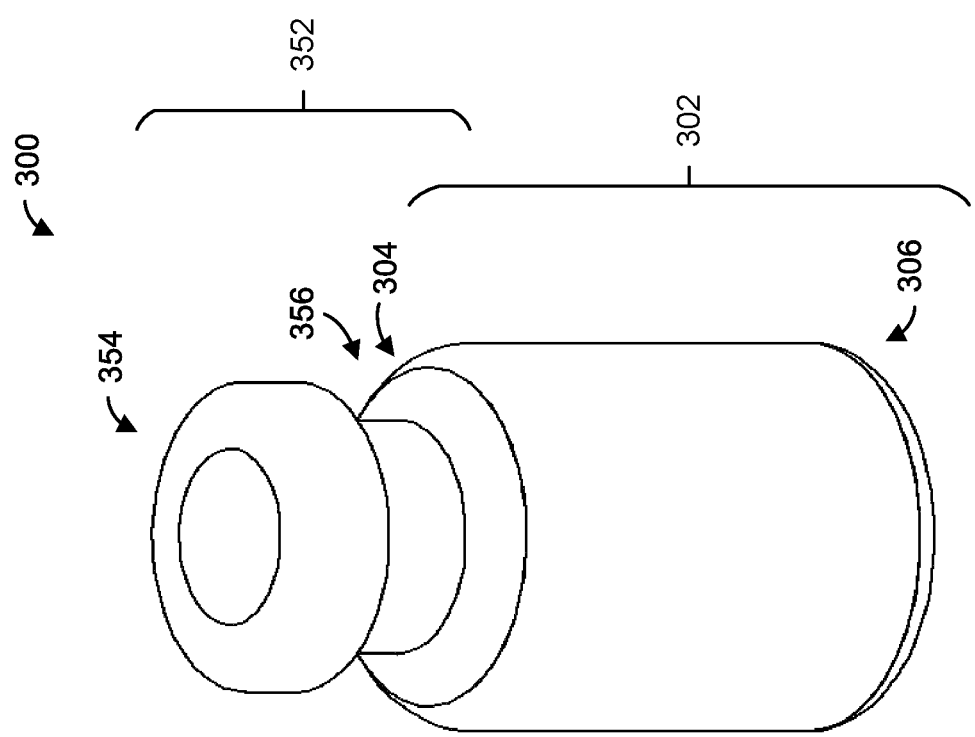
FIG. 3A is a perspective view of an example axial force measurement device in accordance with an embodiment.
Figure 3C:
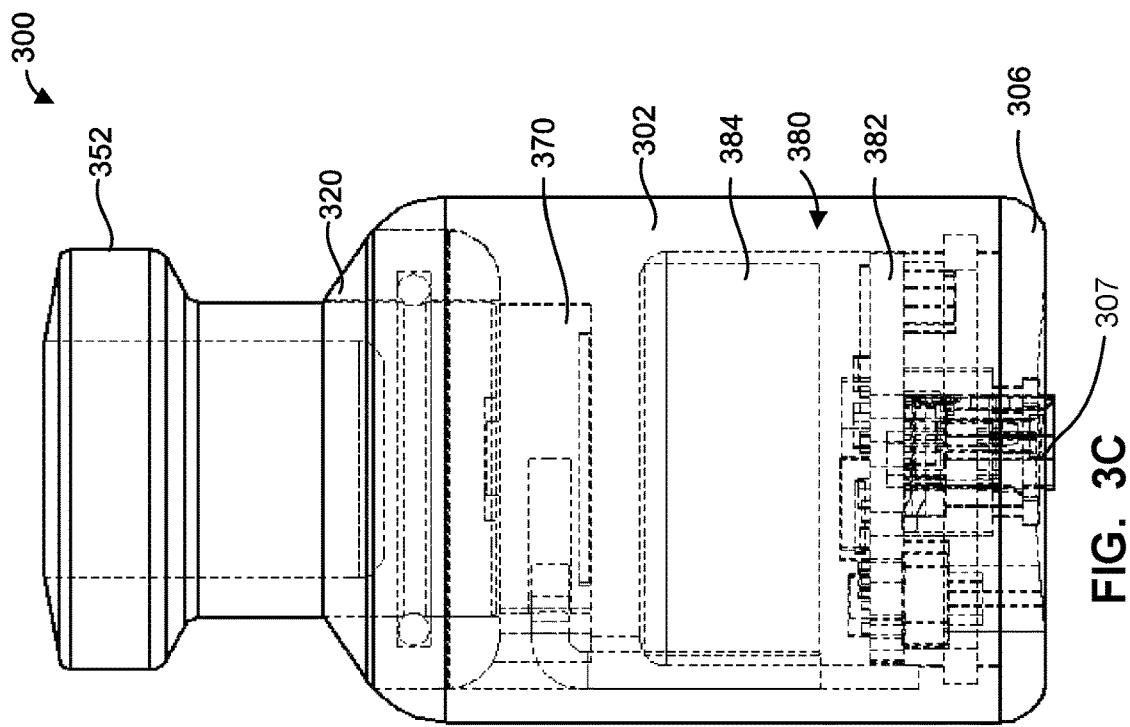
FIG. 3C is a transparent side view of the axial force measurement device shown in FIG. 3A.
Figure 3B:
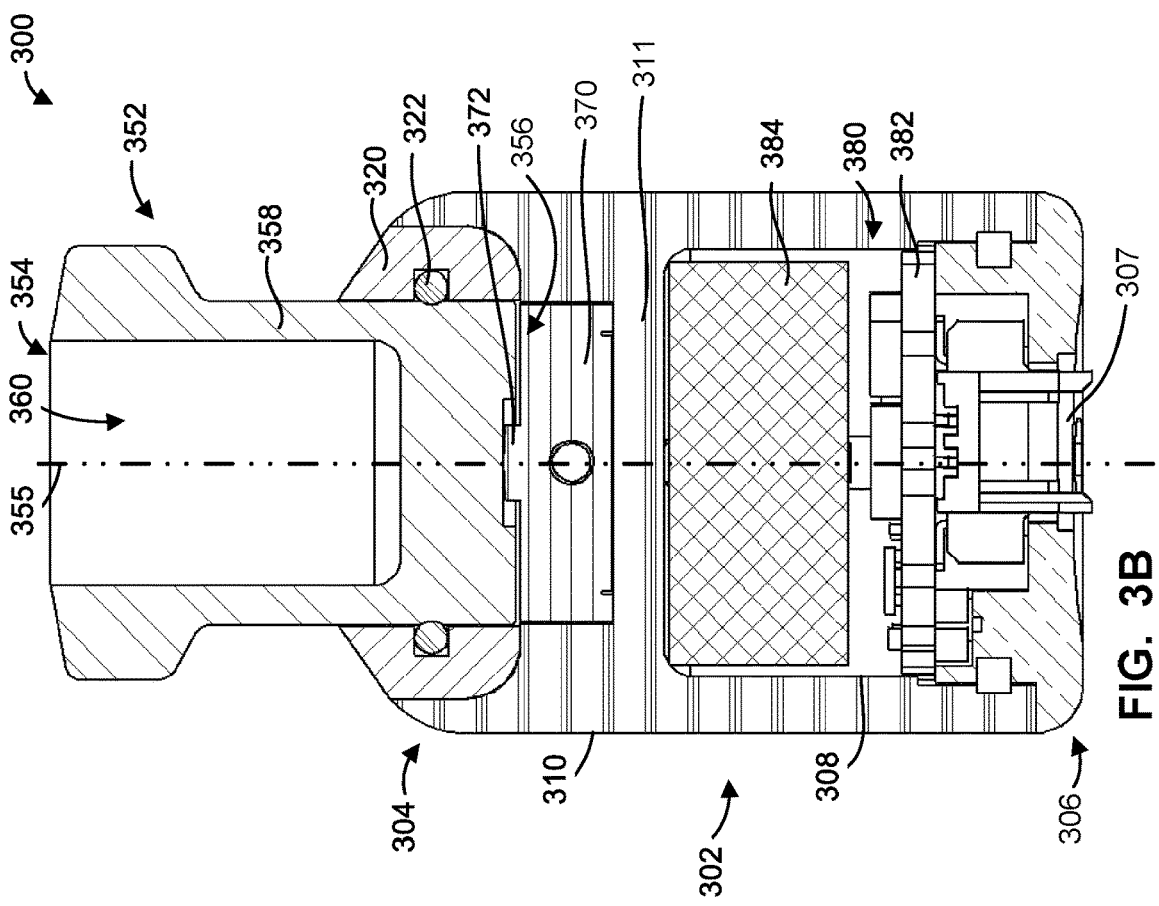
FIG. 3B is a cross-sectional view of the axial force measurement device shown in FIG. 3A.
Figure 3D:
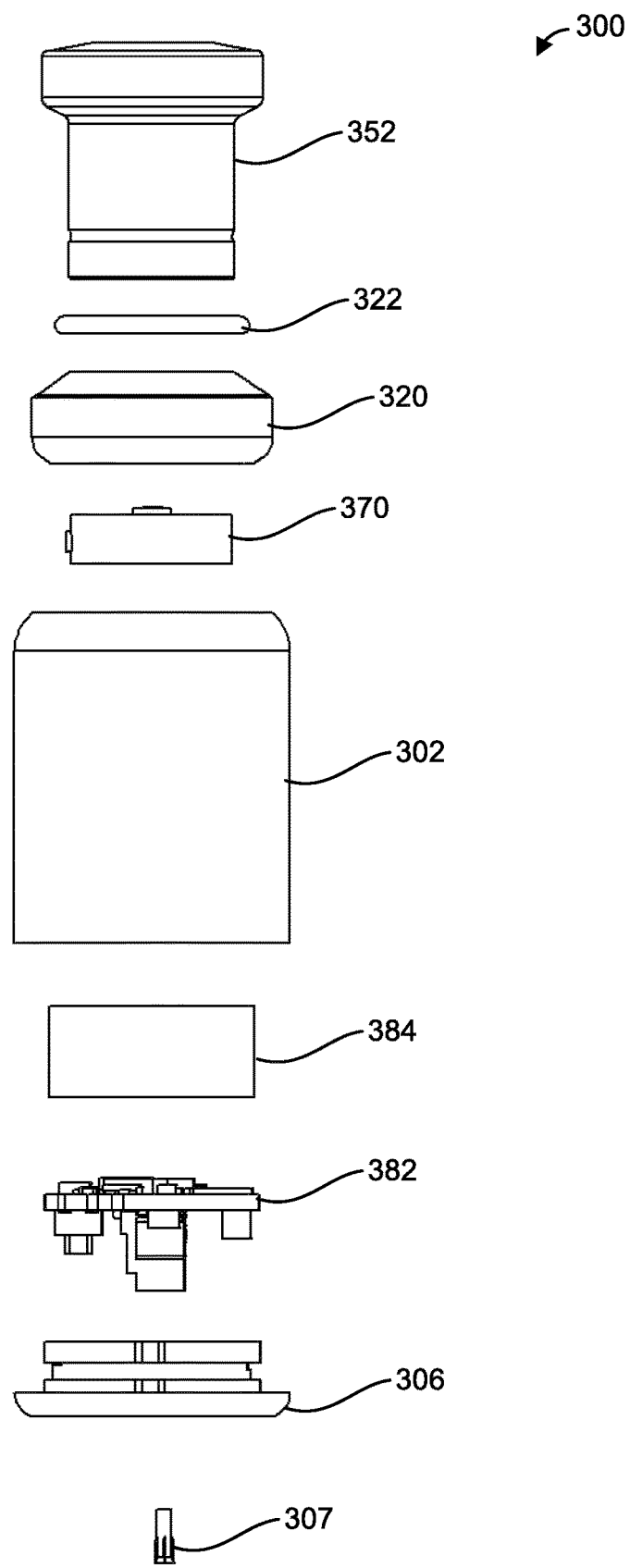
FIG. 3D is an exploded view of the axial force measurement device shown in FIG. 3A.

As shown in FIG. 3A, axial force measurement device 300 can include a device housing section 302 and a container section 352. The container section 352 can be configured to house or contain a product. The device housing section 302 can be configured to house force measurement components usable to measure forces applied to the container section 352.

As shown in FIGS. 3A-3D, container section 352 can extend between a first section end 354 and a second section end 356. The first section end 354 and the second section end 356 can be spaced apart along the longitudinal axis 355 of the device 300. As illustrated, the first section end 354 can be an open first section end and the second section end 356 can be a closed second section end. The container section 352 can include one or more sidewalls 358. The sidewall(s) 358 can extend between the first section end 354 and the second section end 356.

The container section 352 can include a chamber or cavity 360 that is bounded by the first section end 354, the second section end 356, and the sidewall(s) 358. The cavity 360 can be configured to receive a product to be stored by the container, or by the container that the axial force measurement device 300 is intended to emulate. In the example illustrated in FIGS. 3A-D, the cavity 360 is be configured to receive a pharmaceutical product, such as, but not limited to, a solid or liquid medication.

The first section end 354 can be configured to receive a closure member for sealing the cavity 360. The first section end 354 may be configured to receive various types of closure members such as a cap, a plug, a lid etc. In some cases, the first section end 354 can include closure cooperation features configured to cooperate with the closure member to seal the cavity 360. The closure cooperation features may be configured to mate with corresponding mating features provided by the closure member.

For example, the first section end 354 may include a protrusion or lip. The protrusion may be configured to have a portion of the closure member crimped thereupon during a production process. Alternately, the first section end 354 and the closure member may include corresponding engagement members, such as screw threads. The corresponding engagement members can be engaged together during a production process.

Alternately, the first section end 354 may be shaped to receive closure member in a partially inserted position. For example, the closure member may be configured to be partially inserted into the cavity 360 in a friction fit to seal the first section end 354.

In general, the container section 352 can be subject to various axial forces during various stages of a production and/or transportation process. The device housing section 302 can be configured to house various electronic components that can measure the axial forces applied to the container section 352. The device housing section 302 and the container section 352 can have a relatively small size so that the axial force measurement device 300 can mimic the form factor of a relatively small container, such as a pharmaceutical container. For example, the device housing section 302 may have an inner housing diameter of at most 42.5 mm. In some embodiments, the device housing section 302 may have an inner housing diameter of at most 50 mm.

The device housing section 302 can have a first housing end 304 and a second housing end 306. As illustrated the device housing section 302 can extend between the first housing end 304 and the second housing end 306 along the longitudinal axis 355 of the axial force measurement device 300. The device housing section 302 can include an inner housing wall 308 and an outer housing wall 310. The inner housing wall 308 and the outer housing wall 310 can extend between the first housing end 304 and the second housing end 306. As in the example illustrated, the device housing section 302 can house a force measurement sensor 370 and a processing section 380.

The container section 352 can be mounted to the device housing section 302 proximate the first housing end 304. In some examples, container section 352 may be contained within the device housing section 302. In the example illustrated, container section 352 is partially housed within the device housing section 302. That is, the container section 352 extends into the device housing section 302. Alternately, container section 352 may be entirely housed within the device housing section 302. Alternately, container section 352 may be external to the device housing section 302 and connected to the device housing section 302 at the first housing end 304. Alternately, device housing section 302 may be contained (partially or entirely) within the container section 352. That is, the device housing section 302 may extend into the container section 352.

In some examples, container section 352 can be movably mounted so that the container section 352 can move relative to the device housing section 302. For example, container section 352 may be movably mounted to the device housing section 302 via a mounting unit 320. The mounting unit 320 can be secured to the device housing section 302 between the inner housing wall 308 and the container section 352. The mounting unit 320 can be configured to receive the container section 352 and couple the container section 352 to the device housing section 302. The mounting unit 320 can be configured to constrain motion of the container section 352 relative to the device housing section 302. For example, the mounting unit 320 may include a bearing sleeve. The surface of the bearing sleeve can limit movement of the container section 352 along the longitudinal axis of the device 300.

In some examples, the mounting unit 320, the container section 352, and the device housing section 302 can be concentric. For example, as shown in the example illustrated in FIGS. 3A-D, the exterior of the container section 352 can be partially surrounded by the mounting unit 320, which can be partially surrounded by the device housing section 302.

The mounting unit 320 can include a sealing member 322. The sealing member 322 can engage the container section 352. The sealing member 322 can seal the container section 352 to the mounting unit 320. The sealing member 322 may impede the ingress of fluid into the interior of the device housing section 302. For example, the sealing member 322 may include a gasket, such as an O-ring. The sealing member 322 may allow for movement of the container section 352, while sealing and protecting any electrical components within the device housing section 302.

A force measurement sensor 370 and a processing section 380 can be housed within the device housing section 302. The force measurement sensor 370, processing section 380, and the container section 352 can be arranged in various ways. For example, the container section 352, the processing section 380, and the sensor 370 may be arranged linearly within the housing 302. In some cases, the container section 352, the processing section 380, and the sensor 370 may be substantially aligned along the longitudinal axis of the device 300.

The force measurement sensor 370 can be positioned within the device housing section 302 proximate the second section end 356 of the container section 352. The force measurement sensor 370 can be positioned to generate force measurement data in response to an axial force applied at the first section end 354 of the container section 352.

In some examples, when an axial force is applied at the first section end 354, the container section 352 can be urged to move toward the second housing end 306 along the longitudinal axis. The force measurement sensor 370 can be positioned to deflect in response to the motion of the second section end 356 toward the second housing end 306 and generate the force measurement data in response to the deflection. In some cases, the force measurement sensor 370 may be provided by a load cell that includes a button 372 extending towards the second section end 356. The button 372 can be positioned so that the button 372 deflects in response to movement of the second section end 356 toward the second housing end 306.

In some examples, the container section 352 can be made of a rigid material, such as, but not limited to, a metal or rigid plastic. The rigid material may improve the transfer of axial forces from the container section 352 to the force measurement sensor 370. The rigid material may also improve the durability of the container section 352. This may help the container section 352 withstand deformation in response to repeated axial forces.

Alternately, the force measurement sensor and/or container section 352 may be configured to deform in response to an axial force is applied at the first section end 354. For example, a strain gauge may be used to detect the axial force.

The processing section 380 can also be positioned within the device housing section 302. The processing section 380 can one or more components configured to receive force measurement data from the force measurement sensor 370. The processing section 380 can one or more components configured to perform processing operations on the received data. The processing section 380 can one or more components configured to transmit the received data and/or processed data. For example, the processing section 380 can include a processor 382 such as processor 202 described herein above. Processor 382 can be configured to receive force measurement data from the force measurement sensor 370. The processing section 380 may also include a battery 384. Battery may be configured to supply electrical power to various components of the processing section 380, such as the processor 382. The various components of the processing section 380 can be arranged in various ways. For example, in some cases, the battery 384 may be positioned between the processor 382 and the force measurement sensor 370.

Figure 4B:
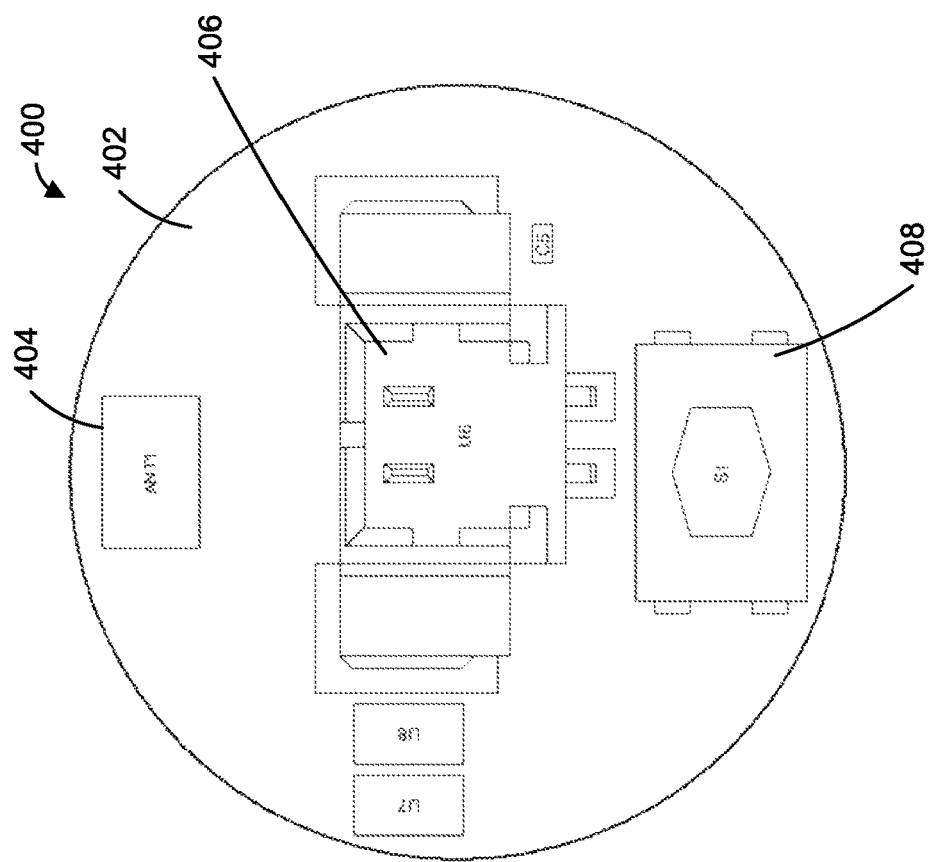
FIG. 4B is a bottom view of the circuit board shown in FIG. 4A.
Figure 4A:
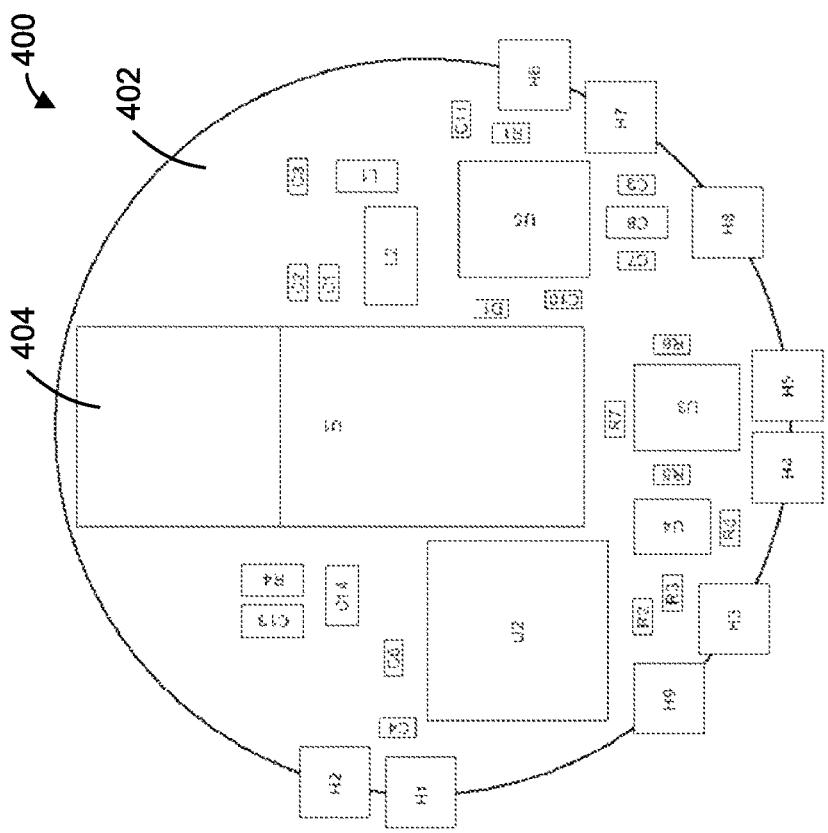
FIG. 4A is a top view of an example circuit board that may be used with the axial force measurement devices of FIGS. 2 and 3A in accordance with an embodiment.

In some examples, one or more components of the processing section 380 can be implemented using a printed circuit board. For example, FIGS. 4A and 4B show an example printed circuit board 400 that may be used to provide various components of the processing section 380. The printed circuit board 400 can include a substrate 402. The substrate 402 can mechanically support and electrically connect various electrical components within the processing section 380. In some cases, the components can be provided by one or more integrated circuits 404 which are mounted to the substrate 402. The printed circuit board 400 may include a charging port 406 coupled to a rechargeable battery within the device 300. The charging port 406 can be configured to be coupled to an external power source to recharge the rechargeable battery. The printed circuit board 400 may also include a power activation input usable to activate/deactivate/reset the device 300. For example, a toggle switch 408 may provide the power activation input. Optionally, the printed circuit board 400 may include a visual output device, such as an LED (not shown).

Referring again to FIGS. 3A-D, the force measurement sensor 370 may be spaced apart from processing section 380. For example, a support member 311 may be positioned between the processing section 380 and force measurement sensor 370. The support member 311 can support the sensor 370 adjacent the second section end 356 of the container section 352. The support member 311 can reduce or prevent axial forces from being transferred from the force measurement sensor 370 to the processing section 380, to minimize or prevent damage to the processing section 380.

As shown in the example illustrated, device housing section 302 can include one or more apertures 307 proximate the second housing end 306. The aperture(s) 307 can define one or more channels from the exterior of the second housing end 306 into the interior of the device housing section 302. The aperture(s) 307 can provide a user with access to the various components housed within the device housing section 302 that may otherwise be difficult to access. For example, the aperture(s) 307 may facilitate recharging the device 300, and/or accessing force measurement data stored on the device, for example, by inserting a cable (e.g. a USB connector cable) to a connector port provided in the device housing section 302. In another example, the aperture(s) 307 may provide access to a switch, such as toggle switch 408, to activate and/or deactivate the device 300. Alternately or in addition, the aperture(s) 307 may provide a passage or pathway to allow light from a visual indicator to be emitted through the housing 302.

Optionally, the second housing end 306 may be removable from the device housing section 302. Removal of the second housing end 306 may provide greater access to the various components stored internally within the device housing section 302, such as a printed circuit board 400, force measurement sensor 370 etc.

In various embodiments, the second housing end 306 may include an extendable section (not shown) that is configured to adjust the overall longitudinal length of the axial force measurement device 300. The extendable section can extend and retract along the longitudinal axis 355 of the device 300 to adjust the longitudinal length of the device 300. The extendable section may allow the axial force measurement device 300 to imitate the form factor of containers having different longitudinal lengths or heights.

The extendable section can include a fixed portion and an adjustable portion, such as a rotatable portion. The rotatable portion can be rotatably mounted to the fixed portion. For example, the rotatable portion can be configured to rotate about the longitudinal axis 355 of device 300. By rotating the rotatable portion about the longitudinal axis 355, the extendable section can be extended and retracted as desired. In other examples, the adjustable portion may be provided in different manners, for instance as a detachable extender portion.

When the rotatable portion is rotated in a first direction (e.g. clockwise in an example), the extendable section can extend along the longitudinal axis 355, increasing the longitudinal length of the extendable section. Conversely, when the rotatable portion is rotated in a second direction (e.g. counter-clockwise in this example), the extendable section can retract along the longitudinal axis 355, decreasing the longitudinal length of the extendable section. The fixed portion and the rotatable portion can have corresponding screw threads which convert rotation of the rotatable portion into a linear translation.

Optionally, the extendable section may include a locking member. Locking member can be configured to secure the extendable section at a particular longitudinal length. For example, the locking member may fix or prevent the rotation of the rotatable portion relative to the fixed portion. Fixing the rotation of the rotatable portion can prevent the extension or retraction of the extendable section. For example, the locking member may be provided by a bolt which fixes the rotatable portion relative to the fixed portion.

In various embodiments, the container section 352 may include an outer container section that is configured to emulate the upper portion of a container. The outer container section may be configured to be compatible with equipment along various stages of a production and/or transportation process. For example, the outer container section may adapt the device 300 for various filling, capping, and/or sealing processes. In the example illustrated in FIGS. 3A-D, the outer container section is configured to mimic the top portion of a pharmaceutical container. In some embodiments, the outer container section may be provided by a portion of an actual container the axial force measurement device 300 is intended to emulate. For example, the outer container section may be provided by a cut away portion of an actual pharmaceutical vial. The use of a portion of an actual container may provide greater compatibility with various production and/or transportation processes as compared to a replica.

The outer container section can be positioned proximate to the container section 352. Outer container section can be fixed to the container section 352. For example, outer container section may be attached to the container section 352 by a friction fit, although other suitable attachment mechanisms may be used. In some embodiments, the outer container section may be concentric with the container section 352. This may help outer container section transfer axial forces to the container section 352.

Referring now to FIGS. 5A-C, there is shown another example of an axial force measurement device 500. Similar to the example axial force measurement device 300 illustrated in FIGS. 3A-D, the axial force measurement device 500 includes a container section 552 and a device housing section 502. The axial force measurement device 500 also includes a force measurement sensor 570 and a processing section 580 positioned within the device housing section 502.

However, in contrast to device 300, the axial force measurement device 500 has a different shape or form factor as compared to the axial force measurement device 300. In particular, the axial force measurement device 500 is shaped as a cartridge for an auto-injector device. Axial force measurement device 500 may be implemented with an actual cartridge for an auto-injector device and/or a replica of a cartridge.

In the example of device 300, the force measurement sensor 570 is provided in the form of a strain gauge 570. The strain gauge 570 can be configured to generate force measurement data in response to the deformation of a strain element. The strain element can be positioned to deform in response to axial forces applied to the first end 554 of container section 552. In some examples, the container section 552 itself may incorporate the strain element. For example, the container section 552 may be configured to deform in response to axial forces imparted at the first end 554. Alternately, the strain element may be provided as a separate component configured to deform in response to axial forces imparted at the first end 554.

In the example illustrated in FIGS. 5A-C, the strain element is provided as a separate strain element 574 proximate the second end 556 of the container section 552. The strain element 574 can deform in response to axial forces applied to the container section 552. In particular, an axial force applied to the container section 552 can cause the container section 552 to move toward second housing end 506. The strain element 574 can be positioned to deform in response to this motion.

In other embodiments, the strain element can be provided by the container section 552. In particular, the container section 552 can deform in response to axial forces applied to the container section 552 and the strain gauge 570 can generate force measurement data in response to the deformation. The container section 552 can be rigidly mounted to the device housing section 502 so that the container section 552 is fixed relative to the device housing section 502.

In some cases, the strain element may be a replaceable component. The strain element may deteriorate over time as the strain element is repeatedly deformed. The strain element may be removed and replaced by another strain element in the event the original strain element has degraded.

Figure 6:
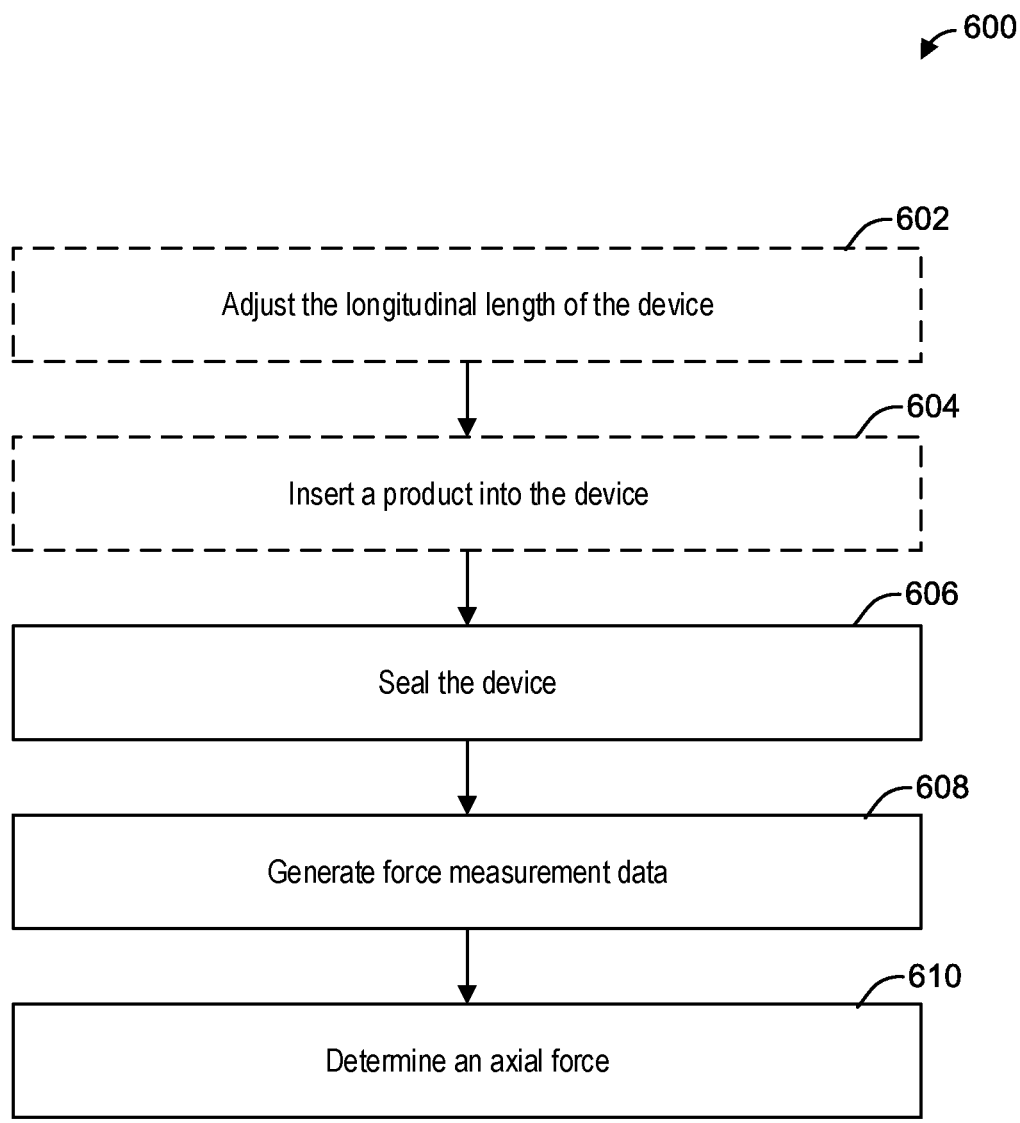
FIG. 6 is a flowchart of an example method for measuring axial forces in accordance with an embodiment.

Referring to FIG. 6, there is shown a flowchart of an example method 600 for measuring axial forces. The method 600 may be implemented using various types of axial force measurement devices, such as the example axial force measurement devices 102, 200, 300, and 500 shown and described herein.

Optionally, at 602 the longitudinal length of the axial force measurement device can be adjusted. The longitudinal length of the axial force measurement device can be adjusted to provide the device with a desired longitudinal length for a force measurement process. For example, the longitudinal length may be defined so that the axial force measurement device imitates the form factor of a particular container it is intended to replicate. The longitudinal length may also be adjusted to ensure compatibility between the axial force measurement device and various stages of a production and/or transportation process.

In some examples, the longitudinal length of the axial force measurement device can be adjusted by replacing the container section of that device. For example, referring to FIGS. 3A-D, the container section 352 can be replaced with another container section (not shown) having a different longitudinal length. Container section 352 may be removed from the first housing end 304 of the device housing 302 and a different container section can be mounted to device housing 302. The replacement container section can be selected to provide device 300 with a desired overall longitudinal length.

Alternately, the longitudinal length of the axial force measurement device can be adjusted by adjusting an extendable section of that device. For example, the extendable section may be extended or retracted so that the device 300 has a desired overall longitudinal length.

Alternately, the longitudinal length of the axial force measurement device may not be adjusted. For example, the device may have a fixed longitudinal length in some examples.

Optionally, at 604 a product can be inserted into the axial force measurement device. For example, referring to FIGS. 3A-D, a product can be inserted into the cavity 360 of the container section 352. The type of product received by the device can depend on the type of container the device is intended to measure forces for. For example, the product may be a pharmaceutical product, a beverage product, a food product, a cosmetic product, etc. In some cases, the product may be a solid. Alternately, the product may be a liquid. The product can be inserted by one or more pieces of equipment in a production process.

Alternately, the axial force measurement device may not have a product inserted therein. This may allow the device to evaluate forces applied to an actual container without wasting product that might otherwise be useable or saleable.

At 606, the axial force measurement device can be sealed. The axial force measurement device can be sealed to enclose the chamber of the container section. The sealing process may be that used to enclose a product within the device. For example, referring to FIGS. 3A-D, a closure member can be applied to the first section end 354 of the container section 352 to seal the cavity 360.

The closure member may be applied by one or more pieces of equipment on a production process. For example, a lid or cap may be inserted into the first section end 354 and secured through a friction fit. Alternately, a lid closure or end wall may be fixed to the first section end 354 through a crimping process for example.

At 608, the axial force measurement device can generate force measurement data. The force measurement sensor can be configured to detect axial forces applied to the device. The sensor may generate force measurement data in response to the axial forces.

For example, the axial force measurement device can generate force measurement data in response to the insertion of the product into the axial force measurement device. Alternately or in addition, the axial force measurement device can generate force measurement in response to the sealing of the axial force measurement device. The insertion of the product and/or the sealing of the device can apply various axial forces to the device, which can be measured as force measurement data. For example, during insertion of the product into the axial force measurement device, a portion of a filling machine will typically come into contact with the axial force measurement device. The axial force measurement device can measure the force applied by the filing machine coming into contact with the axial force measurement device.

At 610, an axial force can be determined. The axial force can be determined based on the force measurement data. In some cases, the axial force measurement device can determine the axial force, for example, using a local processor. Alternately or in addition, the force measurement data can be transmitted to an analysis system, which can determine the axial force. Determining the axial force may, in some embodiments, involve calibrating the force measurement data based on one or more parameters specific to the axial force measurement device.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments. Furthermore, this description is not to be considered as limiting the scope of these embodiments in any way, but rather as merely describing the implementation of these various embodiments.

The invention claimed is:

1. A device for detecting axial forces applied to a container, the device comprising:
   a device housing extending between a first housing end and a second housing end along a longitudinal axis, the device housing having an inner housing wall and an outer housing wall;
   a container section mounted to the housing proximate the first housing end, the container section having an open first section end, a closed second section end, and at least one sidewall extending between the first section end and the second section end, wherein the container section defines a cavity bounded by the first section end, the second section end and the at least one sidewall, and wherein the first end is spaced apart from the second end along the longitudinal axis;
   a force measurement sensor positioned within the device housing, wherein the force measurement sensor is configured to generate force measurement data; and
   a processing section positioned within the housing, the processing section comprising:
      a processor configured to receive the force measurement data from the sensor; and
      a battery configured to supply electrical power to the processor;
   wherein the force measurement sensor is positioned to generate the force measurement data in response to an axial force applied at the first section end.

2. The device of claim 1, wherein the force measurement sensor is positioned proximate the second section end.

3. The device of claim 1, wherein:
   the container section is movable towards the second housing end along the longitudinal axis in response to force applied at the first section end; and
   the force measurement sensor is positioned to deflect in response to motion of the second closed end towards the second housing end and to generate the force measurement data in response to the deflection.

4. The device of claim 3, further comprising a mounting unit fixedly secured to the housing between the inner housing wall and the container section, wherein the mounting unit is configured to receive the container section and to constrain the longitudinal motion of the container section.

5. The device of claim 4, wherein the mounting unit comprises a bearing sleeve.

6. The device of claim 4, wherein the mounting unit comprises a sealing member configured to engage the container section and to seal the container section to the mounting unit.

7. The device of claim 6, wherein the sealing member is configured to impede ingress of fluid into the housing.

8. The device of claim 4, wherein the mounting unit, container section and housing are concentric.

9. The device of claim 1, wherein the force measurement sensor is positioned between the container section and the processing section.

10. The device of claim 9, wherein the force measurement sensor is spaced apart from the processing section.

11. The device of claim 10 further comprising a support member extending between the force measurement sensor and the processing section, wherein the support member supports the force measurement sensor adjacent to the second section end.

12. The device of claim 9, wherein the processor is provided by a printed circuit board, and the battery is positioned between the printed circuit board and the force measurement sensor.

13. The device of claim 12, wherein the device housing comprises at least one aperture at the second housing end, the at least one aperture defining a channel from the second housing end to the printed circuit board.

14. The device of claim 3, wherein the force measurement sensor comprises a load cell.

15. The device of claim 14, wherein:
   the load cell comprises a button extending from the load cell toward the second section end; and
   the button is positioned to deflect in response to movement of the second section end towards the second housing end.

16. The device of claim 1, wherein the first section end is configured to receive a closure member configured to seal the cavity.

17. The device of claim 1, wherein the second housing end comprises an extendable section configured to extend and retract along the longitudinal axis to adjust a longitudinal length of the extendable section.

18. The device of claim 17, wherein the extendable section comprises:
a fixed portion; and
a rotatable portion rotatably mounted to the fixed portion, wherein:
when the rotatable portion is rotated in a first direction, the extendable section extends along the longitudinal axis increasing the longitudinal length of the extendable section, and;
when the rotatable portion is rotated in a second direction, the extendable section retracts along the longitudinal axis, decreasing the longitudinal length of the extendable section.

19. The device of claim 1, wherein the force measurement sensor comprises a strain gauge.

20. The device of claim 19, wherein:
the strain gauge comprises a strain element positioned to deform in response to motion of the second closed end towards the second housing end; and
the strain gauge is configured to generate the force measurement data in response to the deformation of the strain element.

21. The device of claim 19, wherein:
the container section is configured to deform in response to the axial force applied to the container section; and
the strain gauge is configured to generate the force measurement data in response to the deformation of the container section.

22. A method for measuring axial sealing forces using the device of claim 1, the method comprising:
applying a closure member to the first section end to seal the cavity;
generating force measurement data in response the application of the closure member; and
determining an axial force of the application of the closure member using the force measurement data.

23. A device for detecting axial forces applied to a container, the device comprising:
a device housing extending between a first housing end and a second housing end along a longitudinal axis, the device housing having at least one sidewall extending between the first housing end and the second housing end;
a container section mounted to the housing proximate the first housing end, the container section having an open first section end, a closed second section end, and at least one sidewall extending between the first section end and the second section end, wherein the container section defines a cavity bounded by the first section end, the second section end; and
a force measurement sensor positioned within the device housing, the force measurement sensor configured to generate force measurement data, wherein the force measurement sensor is positioned to generate the force measurement data in response to an axial force applied at the first section end.

24. A device for detecting axial forces applied to a container, the device comprising:
a device housing extending between a first housing end and a second housing end along a longitudinal axis, the device housing having an inner housing wall and an outer housing wall;
a container section mounted to the housing proximate the first housing end and extending into the device housing, the container section having an open first section end, a closed second section end, and at least one sidewall extending between the first section end and the second section end, wherein the container section defines a cavity bounded by the first section end, the second section end and the at least one sidewall, and wherein the first end is spaced apart from the second end along the longitudinal axis;
a force measurement sensor positioned within the device housing, wherein the force measurement sensor is configured to generate force measurement data; and
a processing section positioned within the housing, the processing section comprising:
a processor configured to receive the force measurement data from the sensor; and
a battery configured to supply electrical power to the processor;
wherein the force measurement sensor is positioned to generate the force measurement data in response to an axial force applied at the first section end.

* * * * *